(12) United States Patent
Morimoto et al.

(10) Patent No.: US 10,416,319 B2
(45) Date of Patent: Sep. 17, 2019

(54) CERAMIC SCINTILLATOR ARRAY, METHOD FOR MANUFACTURING SAME, RADIATION DETECTOR AND RADIATION INSPECTION DEVICE

(71) Applicants: KABUSHIKI KAISHA TOSHIBA, Tokyo (JP); TOSHIBA MATERIALS CO., LTD., Yokohama-Shi (JP)

(72) Inventors: Kazumitsu Morimoto, Yokohama (JP); Yukihiro Fukuta, Yokohama (JP); Akihisa Saito, Yokohama (JP); Hiroyasu Kondo, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 0 days.

(21) Appl. No.: 15/907,605

(22) Filed: Feb. 28, 2018

(65) Prior Publication Data
US 2018/0188387 A1    Jul. 5, 2018

Related U.S. Application Data

(63) Continuation of application No. PCT/JP2016/083348, filed on Nov. 10, 2016.

(30) Foreign Application Priority Data

Nov. 12, 2015  (JP) .................. 2015-222302

(51) Int. Cl.
*G01T 1/20* (2006.01)
*G21K 4/00* (2006.01)
(Continued)

(52) U.S. Cl.
CPC ............ *G01T 1/2002* (2013.01); *A61B 6/032* (2013.01); *A61B 6/4208* (2013.01); *G01T 1/20* (2013.01);
(Continued)

(58) Field of Classification Search
CPC ....... G01T 1/2002; G01T 1/20; G01T 1/2023; G01T 7/00; A61B 6/00; G21K 4/00; C09K 11/7713
See application file for complete search history.

(56) References Cited

U.S. PATENT DOCUMENTS

| 5,866,908 A | 2/1999 | Novak |
| 6,362,481 B1 * | 3/2002 | Warren ................. G01N 23/083 250/361 R |

(Continued)

FOREIGN PATENT DOCUMENTS

| JP | 2003-262678 A1 | 9/2003 | |
| JP | 2003262678 A * | 9/2003 | ............... G01T 1/20 |

(Continued)

OTHER PUBLICATIONS

Nagano et al., English Translation, obtained Sep. 24, 2018, Google Patent Translation, pp. 1-4 (Year: 2018).*
International Search Report and Written Opinion (Application No. PCT/JP2016/083348) dated Jan. 24, 2017.

*Primary Examiner* — David P Porta
*Assistant Examiner* — Jeremy S Valentiner
(74) *Attorney, Agent, or Firm* — Burr & Brown, PLLC

(57) ABSTRACT

A ceramic scintillator array of an embodiment includes: a plurality of scintillator segments each composed of a sintered compact of a rare earth oxysulfide phosphor; and a reflective layer interposed between the scintillator segments adjacent to each other. The reflective layer contains a transparent resin and reflective particles dispersed in the transparent resin. The reflective particles contain titanium oxide and at least one inorganic substance selected from the group consisting of alumina, zirconia, and silica. A glass transition point of the transparent resin is 50° C. or higher, (Continued)

and a thermal expansion coefficient of the transparent resin at a temperature higher than the glass transition point is $3.5 \times 10^{-5}/°$ C. or less.

14 Claims, 3 Drawing Sheets

(51) Int. Cl.
*G01T 1/202* (2006.01)
*G01T 7/00* (2006.01)
*A61B 6/03* (2006.01)
*A61B 6/00* (2006.01)
*C09K 11/77* (2006.01)

(52) U.S. Cl.
CPC .............. *G01T 1/2023* (2013.01); *G01T 7/00* (2013.01); *G21K 4/00* (2013.01); *C09K 11/7713* (2013.01); *G21K 2004/06* (2013.01)

(56) References Cited

U.S. PATENT DOCUMENTS

| 2003/0236388 | A1 | 12/2003 | Armstrong et al. |
| 2005/0107580 | A1* | 5/2005 | Armstrong ............. C08G 59/18 528/418 |
| 2012/0138874 | A1* | 6/2012 | Yuan ...................... C09K 11/02 252/582 |
| 2014/0239196 | A1 | 8/2014 | Shoji et al. |
| 2014/0301527 | A1* | 10/2014 | Morimoto ............ G01N 23/046 378/4 |
| 2015/0309190 | A1* | 10/2015 | Kinoshita ............. G01T 1/2018 250/486.1 |

FOREIGN PATENT DOCUMENTS

| JP | 2004-162001 A1 | 6/2004 |
| JP | 4959877 B2 | 6/2012 |
| JP | 2012-187137 A1 | 10/2012 |
| JP | 2014-167404 A1 | 9/2014 |
| WO | 2014/162717 A1 | 10/2014 |

* cited by examiner

US 10,416,319 B2

CERAMIC SCINTILLATOR ARRAY, METHOD FOR MANUFACTURING SAME, RADIATION DETECTOR AND RADIATION INSPECTION DEVICE

CROSS-REFERENCE TO RELATED APPLICATIONS

This application is a continuation of prior International Application No. PCT/JP2016/083348, filed on Nov. 10, 2016 which is based upon and claims the benefit of priority from Japanese Patent Application No. 2015-222302, filed on Nov. 12, 2015; the entire contents of all of which are incorporated herein by reference.

BACKGROUND OF THE INVENTION

1. Field of the Invention

Embodiments described herein generally relate to a ceramic scintillator array and a method for manufacturing the same, a radiation detector, and a radiation inspection device.

2. Description of Related Art

In fields of medical diagnosis, industrial non-destructive inspection and the like, inspection using a radiation inspection device such as an X-ray tomograph (hereinafter, described as an X-ray CT scanner) is carried out. The X-ray CT scanner is composed of an X-ray tube (X-ray source) emitting a fan beam X-ray in a fan shape and an X-ray detector including many X-ray detection elements, the X-ray tube and the X-ray detector being arranged opposed each other with a tomographic surface of an inspection target set as a middle. In the X-ray CT scanner, the X-ray tube emits the fan beam X-ray while rotating with respect to the inspection target, and the X-ray detector collects absorption data on X-ray transmitted through the inspection target. Thereafter, the X-ray absorption data is analyzed by a computer, whereby a tomogram is reproduced. For the radiation detector of the X-ray CT scanner, a detection element using a solid scintillator is widely used. In the radiation detector including the detection element using the solid scintillator, it is easy to increase the number of channels by downsizing the detection element, thus further increasing the resolution of the X-ray CT scanner and the like.

The radiation inspection device such as the X-ray CT scanner is used in various fields for medical purpose, industrial purpose and so on. As the X-ray CT scanner, for example, there is a known device of a multi-splice type in which detection elements such as photodiodes are vertically and horizontally arranged in two dimensions and a scintillator array is mounted thereon. Employing the multi-splice type makes it possible to superpose cross-sectional images, thereby three-dimensionally expressing the CT image. The radiation detector mounted in the radiation inspection device includes detection elements arranged in a plurality of vertical and horizontal lines, and each of the detection elements is provided with a scintillator segment. The X-ray incident on the scintillator segment is converted into visible light, and the detection element converts the visible light into an electric signal to image it. In recent years, to obtain high resolution, the detection element is downsized and the pitch between adjacent detection elements is reduced. Accompanying the above, the size of the scintillator segment is also reduced.

Among the various kinds of scintillator materials used for the above-described scintillator segment, a rare earth oxysulfide-based phosphor ceramics is high in light emission efficiency and has preferable characteristics for use in the scintillator segment. Therefore, a radiation detector is becoming widely used which is made by combining a ceramic scintillator segment processed by cutout process or grooving process from a sintered compact (ingot) of the rare earth oxysulfide-based phosphor ceramics being the scintillator material and a photodiode as the detection element.

As the scintillator using the phosphor ceramics, there is a known ceramic scintillator composed of a sintered compact of, for example, a gadolinium oxysulfide phosphor. The ceramic scintillator array is fabricated as follows for instance. First, the rare earth oxysulfide-based phosphor powder being the scintillator material is molded into a suitable shape, and the molded powder is sintered into a sintered compact (ingot). The sintered compact of the scintillator material is subjected to a cutting process such as cutout process or grooving process to form scintillator segments corresponding to the plurality of detection elements. Further, a reflective layer is formed between the scintillator segments to integrate them, thereby fabricating a scintillator array.

In the case of using the above-described ceramic scintillator array as a radiation detector, the dimensional accuracy of the ceramic scintillator array affects the resolution of a CT diagnostic image. Further, a temperature of 50° C. at maximum is applied to the radiation detector mounted on the X-ray CT scanner. In the scintillator array having the reflective layer containing a resin, expansion of the reflective layer due to heating and contraction due to a decrease in temperature occur to cause a small dimensional change between adjacent scintillator segments, namely, pitch shift of the segment, warpage of the scintillator array, variation in outside dimension and so on. These become a cause of deteriorating the resolution of the diagnostic image of the radiation detector. In progress of increase in resolution of the diagnostic image of the radiation detector, a scintillator array having a smaller dimensional change amount due to heating and cooling is required. Further, since the area of the scintillator array also increases with an increase in detection area of the radiation detector, the control of the dimensional change amount due to heating and cooling is important.

Further, the radiation detector mounted on the X-ray CT scanner is exposed to an X-ray during operation. For example, in the case of undergoing exposure to the X-ray for a long period such as 10 years in total, the resin contained in the reflective layer constituting the scintillator array changes in color, resulting in decreased light output. Besides, in the case where the X-ray CT scanner is exposed to a hot and humid atmosphere, the thermal expansion rate of the resin contained in the reflective layer of the scintillator array fluctuates under the influence of the temperature and humidity, resulting in occurrence of the dimensional change of the scintillator array such as pitch shift of the segment, warpage of the scintillator array, variation in outside dimension and so on.

SUMMARY OF THE INVENTION

A ceramic scintillator array of an embodiment includes: a plurality of scintillator segments each composed of a sintered compact of a rare earth oxysulfide phosphor; and a reflective layer interposed between the scintillator segments adjacent to each other in a manner to integrate the plurality of scintillator segments. In the ceramic scintillator array of the embodiment, the reflective layer contains a transparent resin and reflective particles dispersed in the transparent resin. The reflective particles contain titanium oxide and at least one inorganic substance selected from the group consisting of alumina, zirconia, and silica. A glass transition point of the transparent resin is 50° C. or higher, and a thermal expansion coefficient of the transparent resin at a temperature higher than the glass transition point is $3.5 \times 10^{-5}/°$ C. or less.

Hereinafter, embodiments for implementing a ceramic scintillator array, a radiation detector, and a radiation inspection device of the present invention will be described.

CERAMIC SCINTILLATOR ARRAY

Figure 1:
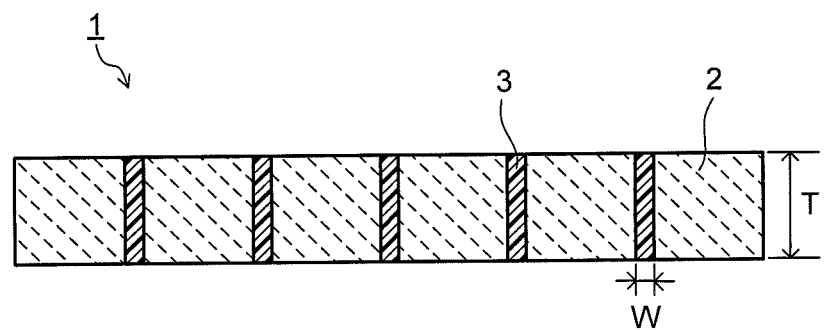
FIG. 1 is a cross-sectional view illustrating a ceramic scintillator array of an embodiment.
Figure 2:
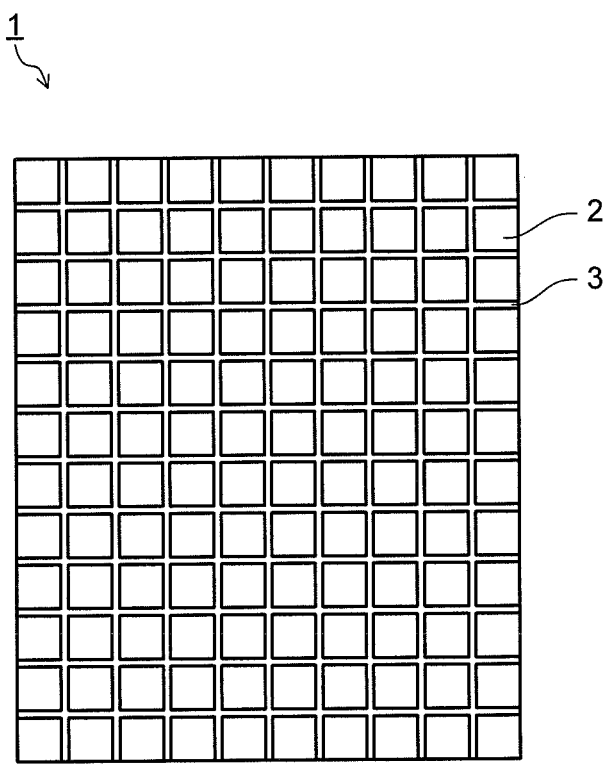
FIG. 2 is a plan view illustrating the ceramic scintillator array of the embodiment.

FIG. 1 is a cross-sectional view illustrating a ceramic scintillator array of an embodiment, and FIG. 2 is a plan view illustrating the ceramic scintillator array of the embodiment. In these drawings, 1 denote a scintillator array, 2 denotes a scintillator segment, and 3 denotes a reflective layer. The scintillator array 1 has a plurality of scintillator segments 2. Between adjacent scintillator segments 2, the reflective layer 3 is interposed. The reflective layer 3 is bonded to each of the adjacent scintillator segments 2. The plurality of scintillator segments 2 are integrated by the reflective layers 3 bonded to them. In other words, the scintillator array 1 has a structure in which the plurality of scintillator segments 2 are integrated by the reflective layers 3.

The scintillator array 1 may have any one of a structure in which the plurality of scintillator segments 2 are arranged in a line and a structure in which the plurality of scintillator segments 2 are arranged in two dimensions with a predetermined number of the scintillator segments 2 arranged each in a vertical direction and a horizontal direction as illustrated in FIG. 2. In the case where the plurality of scintillator segments 2 are arrayed in two dimensions, the reflective layer 3 is provided between the scintillator segments 2 in each of the vertical direction and the horizontal direction. The number of scintillator segments 2 is appropriately set according to the structure, resolution or the like of the radiation detector such as an X-ray detector.

The scintillator segment 2 is composed of a sintered compact of a rare earth oxysulfide phosphor. An example of a rare earth oxysulfide phosphor ceramics is a rare earth oxysulfide phosphor containing praseodymium (Pr) as an activator. Examples of the rare earth oxysulfide constituting a phosphor ceramics include oxysulfides of rare earth elements such as yttrium (Y), gadolinium (Gd), lanthanum (La), lutetium (Lu) and so on.

The scintillator segment 2 in the ceramic scintillator array 1 of the embodiment is preferably composed of a rare earth oxysulfide phosphor ceramics (scintillator material) having a composition expressed by general formula:

$$RE_2O_2S:Pr \qquad (1)$$

where RE is at least one element selected from the group consisting of Y, Gd, La, and Lu.

Gd, in particular, of the above-described rare earth elements has a large X-ray absorption coefficient and contributes to improvement in light output of the ceramic scintillator array 1. Accordingly, it is more preferable to use $Gd_2O_2S:Pr$ phosphor for the scintillator segment 2 of the embodiment. Note that another rare earth element may substitute for a part of Gd. In this case, a substitution amount of another rare earth element for Gd is preferably set to 10 mol % or less.

More specifically, in the ceramic scintillator array 1 of the embodiment, it is desirable to use, for the scintillator segment 2, the rare earth oxysulfide phosphor ceramics substantially expressed by general formula:

$$(Gd_{1-x}RE'_x)_2O_2S:Pr \qquad (2)$$

where RE' is at least one element selected from the group consisting of Y, La, and Lu, and x is a number of atomic ratio satisfying $0 \leq x \leq 0.1$.

In the ceramic scintillator array 1 of the embodiment, praseodymium (Pr) is used as the activator that increases light output of the rare earth oxysulfide phosphor ceramics (scintillator material). Pr can further reduce afterglow or the like as compared with other activators. Accordingly, the rare earth oxysulfide phosphor ceramics (scintillator material) containing Pr as the activator is effective as a fluorescence generating means of the radiation detector.

The content of Pr in the rare earth oxysulfide phosphor ceramics is preferably set to a range of 0.001 to 10 mol % relative to a phosphor host (for example, $RE_2O_2S$ such as $Gd_2O_2S$). A content of Pr exceeding 10 mol % conversely causes a decrease in light output. A content of Pr less than 0.001 mol % fails to provide sufficient effect as a main activator. The content of Pr is preferably in a range of 0.01 to 1 mol %.

In the rare earth oxysulfide phosphor ceramics used in the embodiment, a small amount of at least one element selected from the group consisting of Ce, Zr, and P may be contained as a coactivator in addition to Pr as the main activator. These elements exhibit effect to suppression of exposure deterioration, suppression of afterglow and so on. The contents of the coactivators are preferably set, as a total amount, to a range of 0.00001 to 0.1 mol % relative to the phosphor host.

Further, a scintillator sintered compact forming the scintillator segment 2 of the embodiment is preferably composed of a high-purity rare earth oxysulfide-based phosphor ceramics (scintillator material). Since impurities become a cause of a decrease in sensitivity of the scintillator, it is preferable to reduce as much as possible the impurity amount. In particular, a phosphate radical ($PO_4$) becomes a cause of a decrease in sensitivity, and therefore its content is preferably set to 150 ppm or less. In the case of using fluoride or the like as a sintering aid for densification, the sintering aid remains as an impurity, causing a decrease in sensitivity.

Figure 3:
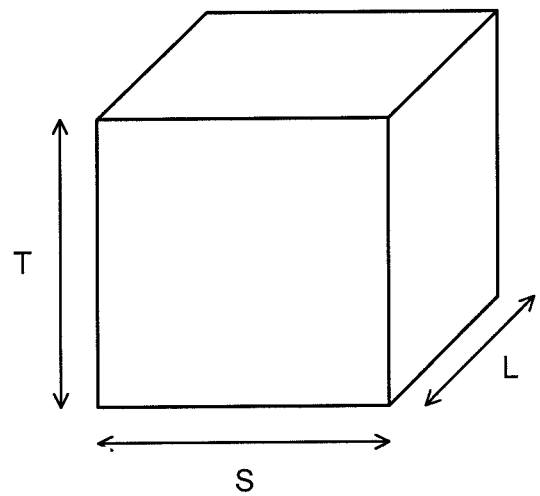
FIG. 3 is a perspective view illustrating a scintillator segment used for the ceramic scintillator array of the embodiment.

The scintillator segment 2 is composed of a sintered compact in a cube shape or a rectangular parallelepiped shape, as illustrated in FIG. 3. The volume of the scintillator segment 2 is preferably 1 $mm^3$ or less. Downsizing the scintillator segment 2 makes it possible to obtain an image to be detected with higher definition. Each size of the length (L), breadth (S) and thickness (T) of the scintillator segment 2 is not always limited, but is preferably 1 mm or less. When the volume of the scintillator segment 2 is downsized to be 1 mm$^3$ or less, the width (W) of the reflective layer 3 can be made smaller to 100 μm or less, and further to 50 μm or less.

In the ceramic scintillator array 1 of the embodiment, the reflective layer 3 that integrates the plurality of scintillator segments 2 contains a transparent resin and reflective particles dispersed in the transparent resin. For the transparent resin, a resin having a glass transition point (transition temperature) of 50° C. or higher is used. Since any of the temperature during process of manufacturing an X-ray CT scanner, the temperature during use of the X-ray CT scanner, and the temperature of a storage environment of the X-ray CT scanner is about 18 to 50° C., it is possible to suppress dimensional change (pitch shift of the segment, warpage of the scintillator array, variation in outside dimension) during manufacturing process, during use, and during storage as long as the glass transition point of the transparent resin is 50° C. or higher. The glass transition point of the transparent resin constituting the reflective layer 3 is preferably higher than 50° C., more preferably 60° C. or higher, and particularly preferably 85° C. or higher.

Further, the thermal expansion coefficient (linear expansion coefficient) at a temperature exceeding the glass transition point of the transparent resin constituting the reflective layer 3 is $3.5 \times 10^{-5}/°$ C. or less. When the thermal expansion coefficient at the temperature exceeding the glass transition point of the transparent resin exceeds $3.5 \times 10^{-5}/°$ C., a change (pitch shift of the segment, warpage of the scintillator array, variation in outside dimension) is likely to occur in finished dimension of the scintillator array due to the temperature during the process of manufacturing the X-ray CT scanner. The thermal expansion coefficient at the temperature exceeding the glass transition point of the transparent resin is more preferably $2.5 \times 10^{-5}/°$ C. or less. The thermal expansion coefficient at a temperature lower the glass transition point of the transparent resin is preferably $2.1 \times 10^{-5}/°$ C. or less, and furthermore preferably $1.6 \times 10^{-5}/°$ C. or less.

To satisfy the above-described glass transition point and thermal expansion coefficient at the temperature exceeding the glass transition point, the transparent resin preferably has a molecular structure including a cyclo structure including no double structure (double bond). In the case where the molecular structure of the transparent resin constituting the reflective layer 3 includes the double structure, the glass transition point is likely to become lower than 50° C., and when the scintillator array 1 is exposed to X-ray of an exposure amount corresponding to 10 years operation, the transparent resin changes in color to yellow and the reflective layer 3 becomes likely to decrease in reflectance. Regarding the decrease in light output of the scintillator array 1, when the initial light output is 100%, the decrease amount possibly exceeds, for example, 25%.

The transparent resin constituting the reflective layer 3 is preferably an epoxy resin having an aliphatic skeleton. Using the epoxy resin having the aliphatic skeleton makes it easier to satisfy the above-described glass transition point and thermal expansion coefficient at the temperature exceeding the glass transition point. Further, the epoxy resin as the transparent resin preferably has the above-described molecular structure including the cyclo structure. Using the epoxy resin makes it easier to increase the glass transition point and lower the thermal expansion coefficient at the temperature exceeding the glass transition point. In addition, the transparent resin is preferably a room temperature setting two-component epoxy resin.

In the reflective layer 3 of the ceramic scintillator array 1 of the embodiment, the reflective particles dispersed in the transparent resin contain titanium oxide ($TiO_2$) and at least one inorganic substance selected from the group consisting of alumina ($Al_2O_3$), zirconia ($ZrO_2$), and silica ($SiO_2$). Using the reflective particles makes it possible to increase the reflectance by the reflective layer 3 with respect to visible light emitted from the scintillator segments 2, and accordingly to increase light output of the scintillator array 1. The mass ratio between the titanium oxide and the above-described inorganic substance is not limited in particular, but is preferably set to a range of titanium oxide: inorganic substance=7:3 to 21:4.

The reflective particles preferably have a bimodal-type particle size distribution. More specifically, the reflective particles preferably have a particle size distribution having a first particle diameter peak and a second particle diameter peak. Further, it is preferable that in the particle size distribution of the reflective particles, the first particle diameter peak exists in a range of 200 to 350 nm and the second particle diameter peak exists in a range of 750 to 1000 nm. In the case where the particle size distribution of the reflective particles is of a unimodal type, the reflection efficiency of the reflective layer 3 with respect to light having a wavelength of 512 nm becomes more likely to decrease. In contrast to the above, using the reflective particles having the above-described bimodal-type particle size distribution can increase the reflection efficiency of the reflective layer 3. Specifically, the reflection efficiency of the reflective layer 3 with respect to light having a wavelength of 512 nm is preferably 90% or more, with which the variation in light output of the ceramic scintillator array 1 can be reduced.

Regarding the ratio between the transparent resin and the reflective particles forming the reflective layer 3, the mass ratio of the transparent resin is preferably 15 to 60%, and the mass ratio of the reflective particles is 40 to 85% (where the mass ratio of the transparent resin+the mass ratio of the reflective particles=100%). When the mass ratio of the reflective particles is less than 40%, the reflection efficiency of the reflective layer 3 decreases, and the reflection efficiency of the reflective layer 3 with respect to light having a wavelength of 512 nm is likely to be lower than 90%. When the mass ratio of the reflective particles exceeds 85%, the reflection efficiency of the reflective layer 3 does not change, but the mass ratio of the transparent resin relatively decreases, resulting in difficulty in stable solidification of the reflective layer 3.

According to the ceramic scintillator array 1 using the above-described reflective layer 3, the change amount in any of pitch, warpage, and outside dimension after the ceramic scintillator array 1 is stored in a packed state for one month in an atmosphere at a temperature of 50° C. and a humidity of 80% RH can be made 0.02 mm or less. By satisfying the change amount, the temporal dimensional change (pitch shift of the segment, warpage of the scintillator array, variation in outside dimension) of the ceramic scintillator array 1 due to influence of temperature, humidity and so on can be suppressed. Accordingly, the ceramic scintillator array 1 with less variation in light output can be provided. Further, because of less change in color of the transparent resin constituting the reflective layer 3 due to the exposure to an X-ray, the decrease in light output of the ceramic scintillator array 1 due to change in color of the transparent resin can be suppressed. For example, the decrease in light output of the ceramic scintillator array 1 by an X-ray exposure amount corresponding to 10 years operation can be made to be within 25%.

The ceramic scintillator array 1 of the embodiment is manufactured as follows for instance. First, the reflective particles and a resin composition in an uncured state constituting the transparent resin (an uncured material of the transparent resin) are prepared and mixed together to prepare a mixture. Then, a plurality of scintillator segments 2 each processed in a predetermined shape are arranged at regular intervals. The above-described mixture of the reflective particles and the resin composition in the uncured state is applied or filled between adjacent scintillator segments 2. The resin composition in the uncured state preferably has a viscosity of 0.2 to 1 Pa·s (200 to 1000 cps). When the viscosity of the resin composition is less than 0.2 Pa·s, the flowability becomes low, resulting in deterioration of the workability of applying or filling between the scintillator segments 2. When the viscosity of the resin composition exceeds 1 Pa·s, the flowability becomes too high, resulting in a decreased in coating performance or filling performance. Further, the total light transmittance of the transparent resin is preferably 85% or more. When the total light transmittance of the transparent resin is less than 85%, the reflection efficiency of the reflective layer 3 becomes more likely to decrease.

The mixture of the reflective particles and the resin composition in the uncured state is applied or filled between the plurality of scintillator segments 2 and then the resin composition in the mixture is cured to form the reflective layer 3, thereby bonding and integrating adjacent scintillator segments 2 to manufacture the ceramic scintillator array 1. The curing processing of the mixture is appropriately set according to the kinds or the like of the resin composition in the uncured state and a curing agent. For example, in the case of a thermosetting resin composition, the curing reaction is promoted by performing thermal processing. In the case of the resin composition such as the two-component epoxy resin, the curing reaction is promoted by leaving the resin composition stand under room temperature.

(Radiation Detector)

Figure 4:
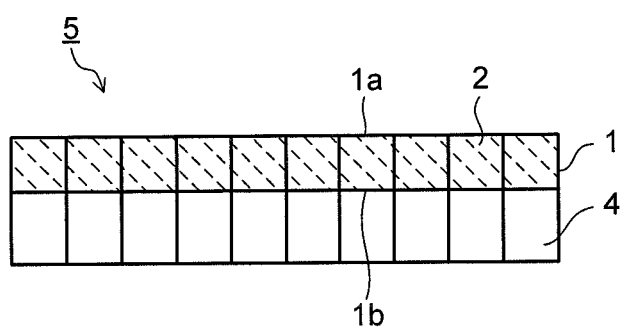
FIG. 4 is a view illustrating a radiation detector of an embodiment.

The radiation detector of an embodiment includes the above-described ceramic scintillator array 1 of the embodiment as a fluorescence generating means that emits light according to an incident radiation ray, and further includes a photoelectric conversion means that receives the light from the fluorescence generating means and converts the light output to an electric output. FIG. 4 illustrates an X-ray detector being one example of the radiation detector of the embodiment. An X-ray detector 5 illustrated in FIG. 4 includes the ceramic scintillator array 1 as the fluorescence generating means and a photoelectric conversion element 4 like a photodiode as the photoelectric conversion means.

The ceramic scintillator array 1 has an X-ray incident surface 1a, and the photoelectric conversion element 4 is integrally mounted on a surface 1b on the opposite side to the X-ray incident surface 1a. As the photoelectric conversion element 4, for example, a photodiode is used. The photoelectric conversion element 4 is arranged to correspond to each of the plurality of scintillator segments 2 constituting the ceramic scintillator array 1. They constitute the radiation detector 5.

The X-ray incident surface 1a of the ceramic scintillator array 1 may be provided with a surface reflective layer. The surface reflective layer is provided not only on the X-ray incident surface 1a of the ceramic scintillator array 1 but may be provided on the mounting surface 1b for mounting the photoelectric conversion element 4. Further, the surface reflective layer may be provided on both the X-ray incident surface 1a and the element mounting surface 1b of the scintillator array 1. Providing the surface reflective layer on the ceramic scintillator array 1 makes it possible to further improve the reflection efficiency with respect to visible light emitted from the scintillator array 1, and accordingly improve the light output of the scintillator array 1. For the surface reflective layer, a mixture of reflective particles and a transparent resin, a lacquer-based coating material or the like is used. The mixture of the reflective particles and the transparent resin preferably has the same constitution as that of the reflective layer 3. The thickness of the surface reflective layer is preferably in a range of 50 to 250 μm. When the thickness of the surface reflective layer is less than 50 μm, sufficient effect of improving the reflection efficiency cannot be obtained. When the thickness of the surface reflective layer exceeds 250 μm, the X-ray amount transmitted decreases, resulting in a decrease in detection sensitivity.

(Radiation Inspection Device)

Figure 5:
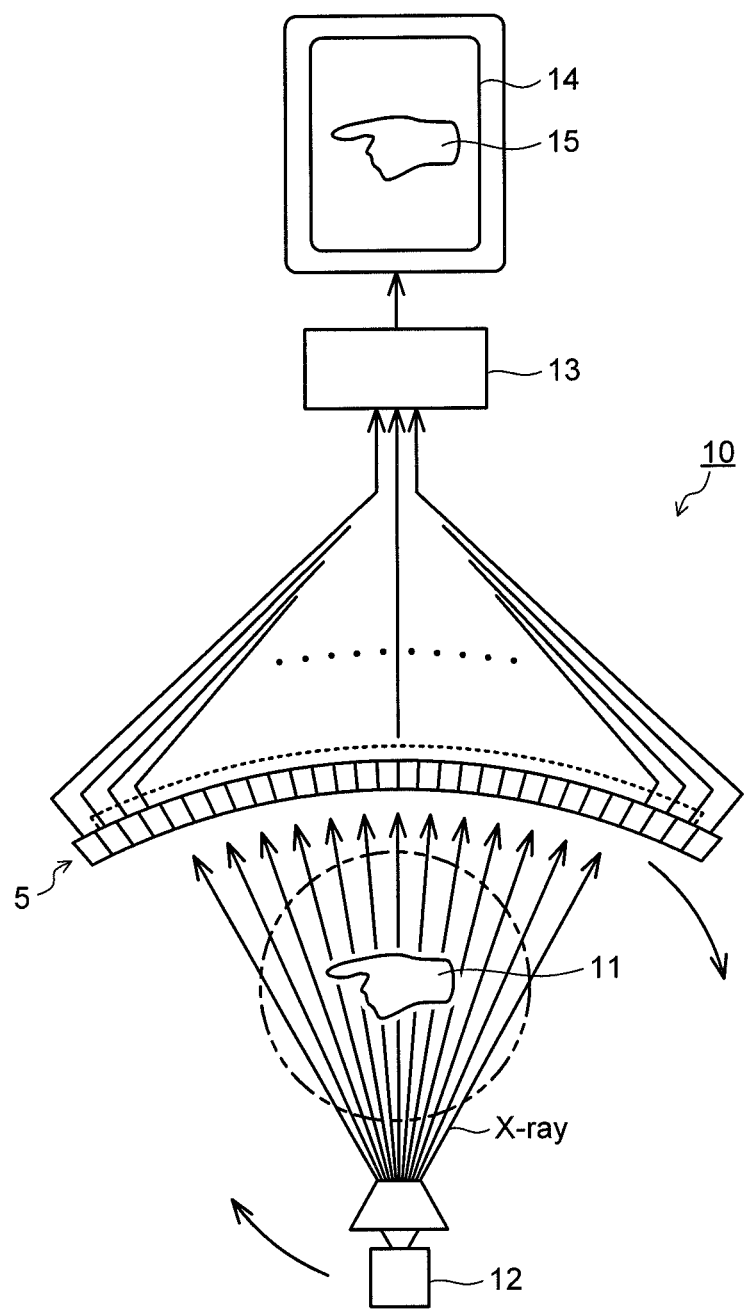
FIG. 5 is a view illustrating a radiation inspection device of an embodiment.

The radiation inspection device of an embodiment includes a radiation source that emits a radiation ray toward an inspection target, and a radiation detector that detects the radiation ray transmitted through the inspection target. For the radiation detector, the above-described radiation detector of the embodiment is used. FIG. 5 illustrates an X-ray CT scanner 10 being an example of the radiation inspection device of the embodiment. In FIG. 5, 10 denotes an X-ray CT scanner, 11 denotes a specimen, 12 denotes an X-ray tube, 13 denotes a computer, 14 denotes a display, and 15 denotes a specimen image. The X-ray CT scanner 10 includes the X-ray detector 5 of the embodiment. The X-ray detector 5 is pasted on, for example, an inner wall surface of a cylinder where an imaged part of the specimen 11 is arranged. At an almost center of an arc of the cylinder where the X-ray detector 5 is pasted, the X-ray tube 12 that emits an X-ray is mounted. Between the X-ray detector 5 and the X-ray tube 12, the specimen 11 is arranged. On the X-ray incident surface side of the X-ray detector 5, a not-illustrated collimator is provided.

The X-ray detector 5 and the X-ray tube 12 are configured to rotate while photographing with the X-ray around the specimen 11. Image information on the specimen 11 is three-dimensionally collected from different angles. Signals obtained by X-ray photography (electric signals converted by the photoelectric conversion element) are processed by the computer 13 and displayed as the specimen image 15 on the display 14. The specimen image 15 is, for example, a tomogram of the specimen 11. Using the scintillator array 1 in which the scintillator segments 2 are two-dimensionally arranged as illustrated in FIG. 4 also makes it possible to constitute a multi-tomogram type X-ray CT scanner 10. In this case, a plurality of tomograms of the specimen 11 are photographed at the same time and, for example, a photographing result can be three-dimensionally drawn.

The X-ray CT scanner 10 illustrated in FIG. 5 includes the X-ray detector 5 including the ceramic scintillator array 1 of the embodiment. As described above, the ceramic scintillator array 1 of the embodiment has excellent light output because the reflection efficiency with respect to visible light emitted from the scintillator segments 2 is high on the basis of the configuration or the like of the reflective layer 3. Using the X-ray detector 5 including the scintillator array 1 makes it possible to shorten the photographing time by the X-ray CT scanner 10. As a result, it is possible to shorten the exposure time of the specimen 11 and achieve reduced exposure. The radiation inspection device (X-ray CT scanner 10) of the embodiment is applicable not only to the X-ray inspection for medical diagnosis of a human body but also to the X-ray inspection for animals, the X-ray inspection for industrial usage and so on. Further, the radiation inspection device also contributes to an improvement in inspection accuracy by an X-ray nondestructive inspection device.

EXAMPLES

Next, concrete examples of the present invention and their evaluation results will be described.

Examples 1 to 3, Comparative Examples 1 to 2

A phosphor powder having a composition of $Gd_2O_2S$:Pr (Pr concentration=0.05 mol %) was temporarily molded by rubber pressing, and a temporarily molded body was enclosed by deaeration in a capsule made of Ta and then set in an HIP processing apparatus. Into the HIP processing apparatus, an argon gas was sealed as a pressurizing medium, and processing was carried out for 3 hours under conditions of a pressure of 147 MPa and a temperature of 1425° C. In the above manner, a sintered compact in a cylindrical shape having a diameter of about 80 mm×a height of about 120 mm was fabricated. From the sintered compact, scintillator segments each having a thickness of 0.7 mm×a width of 0.7 mm×a length of 0.8 mm were cut in a matrix form of 100 segments in the length direction and 30 segments in the width direction to fabricate the ceramic scintillator arrays according to examples and comparative examples.

The ceramic scintillator arrays according to examples and comparative examples were each fabricated by integrating the above-described plurality of scintillator segments via a reflective layer composed of a mixture of 65 mass % of reflective particles and 35 mass % of transparent resin. A reflective layer having a thickness of 0.1 mm was arranged in each of the vertical direction and the horizontal direction of the scintillator array. For the reflective particles, a mixture of 80 mass % of titanium oxide particles and 20 mass % of alumina particles was used. For the transparent resins in Examples 1 to 3, epoxy resins A to C each having a molecular structure of an aliphatic skeleton not including the double structure but including the cyclo structure were used. The glass transition points and the thermal expansion coefficients (linear expansion coefficients) at temperatures higher than the glass transition points of the epoxy resins A to C were adjusted by the molecular structures and are as listed in Table 1. For the transparent resins of Comparative Examples 1 to 2, epoxy resins D, E each having a molecular structure including the double bond were used. The glass transition points and the thermal expansion coefficients (linear expansion rates) at temperatures higher than the glass transition points of the epoxy resins D, E are as listed in Table 1.

TABLE 1

| | Kind of Transparent Resin | Molecular Structure | Glass Transition Point [° C.] | Thermal Expansion Coefficient*1 [×10$^{-5}$/° C.] |
|---|---|---|---|---|
| Example 1 | A | Cyclo Structure | 50 | 3.5 |
| Example 2 | B | Cyclo Structure | 85 | 1.6 |
| Example 3 | C | Cyclo Structure | 65 | 2.4 |
| Comparative Example 1 | D | Double Structure | 45 | 6.2 |
| Comparative Example 2 | E | Double Structure | 20 | 7.1 |

*1 Thermal expansion coefficient at a temperature higher than the glass transition point.

The outside shapes in the long side direction and short side direction, pitch and warpage of each of the scintillator arrays according to Examples 1 to 3 and Comparative Examples 1 to 2 were measured. The measurement results (unit: mm) of the maximum value, minimum value, average value, and standard deviation of the measured values are listed in Table 2 and Table 3. The outside shapes (in the long side direction and in the short side direction) were measured using a micrometer. The pitch was measured using a CNC image measuring system (manufactured by Nikon Corporation, NEXIV, model VMZ-R3020). Regarding the pitch, a shift from a design value of the pitch of the reflective layer was measured using the reflective layer adjacent to an endmost segment as a reference. Regarding the warpage, the warpage amount of the scintillator array in the cross direction was measured using a shape measurement device (manufactured by Mitutoyo Corporation, model CV-500). As listed in Table 2 and Table 3, it is found that the ceramic scintillator arrays in Examples 1 to 3 are smaller in standard deviations of the outside shapes (in the long side direction and in the short side direction), the pitch and the warpage than those in Comparative Examples 1 to 2. Therefore, according to the ceramic scintillator arrays in Examples 1 to 3, the variation in dimension can be reduced to improve the dimensional accuracy.

TABLE 2

| | Dimension Measurement Item (unit: mm) | | | | | | | |
|---|---|---|---|---|---|---|---|---|
| | Outside Shape (Long Side Direction) | | | | Outside Shape (Short Side Direction) | | | |
| | Maximum Value | Minimum Value | Average Value | Standard Deviation | Maximum Value | Minimum Value | Average Value | Standard Deviation |
| Exam. 1 | 89.90 | 89.88 | 89.89 | 0.005 | 23.92 | 23.90 | 23.91 | 0.004 |
| Exam. 2 | 89.92 | 89.90 | 89.91 | 0.003 | 23.92 | 23.90 | 23.91 | 0.002 |
| Exam. 3 | 89.90 | 89.88 | 89.89 | 0.005 | 23.94 | 23.91 | 23.93 | 0.004 |
| Comp. Exam. 1 | 89.92 | 89.88 | 89.90 | 0.009 | 23.92 | 23.89 | 23.91 | 0.007 |
| Comp. Exam. 2 | 89.92 | 89.88 | 89.90 | 0.011 | 23.95 | 23.92 | 23.93 | 0.007 |

TABLE 3

| | Dimension Measurement Item (unit: mm) | | | | | | | |
|---|---|---|---|---|---|---|---|---|
| | Pitch | | | | Warpage | | | |
| | Maximum Value | Minimum Value | Average Value | Standard Deviation | Maximum Value | Minimum Value | Average Value | Standard Deviation |
| Exam. 1 | 0.010 | 0.003 | 0.006 | 0.001 | 0.016 | 0.003 | 0.007 | 0.003 |
| Exam. 2 | 0.009 | 0.002 | 0.004 | 0.001 | 0.008 | 0.003 | 0.005 | 0.001 |
| Exam. 3 | 0.008 | 0.001 | 0.004 | 0.002 | 0.006 | 0.001 | 0.003 | 0.001 |
| Comp. Exam. 1 | 0.019 | 0.002 | 0.008 | 0.004 | 0.036 | 0.001 | 0.016 | 0.008 |
| Comp. Exam. 2 | 0.019 | 0.004 | 0.009 | 0.004 | 0.036 | 0.002 | 0.015 | 0.011 |

Next, the scintillator arrays according to the above-described Examples 1 to 3 and Comparative Examples 1 to 2 were stored in a packed state for one month in an atmosphere at 50° C. and 80% RH, and the outside dimensions, pitch and warpage of each of the scintillator arrays before and after the storage were measured as in the above-described method. Further, exposure to the X-ray of the X-ray exposure amount corresponding to 10 years operation was performed, the light output after the X-ray exposure was measured taking the light output before the X-ray exposure as 100%, and the light output decrease amount (%) was measured. These measurement results are listed in Table 4. As listed in Table 4, it is found that the ceramic scintillator arrays in Examples 1 to 3 are smaller in change amounts of the outside dimensions, pitch, and warpage than those in Comparative Examples 1 to 2, and the decrease amount in light output after the X-ray exposure also decreases. Accordingly, according to the ceramic scintillator arrays in Examples 1 to 3, the change amount in dimension and the decrease amount in light output can be reduced.

TABLE 4

| | Pitch Change Amount After Storage [mm]*1 | Warpage Change Amount After Storage [mm]*1 | Outside Diameter Change Amount After Storage [mm]*1 | Light Output Decrease Amount After X-Ray Exposure [%]*2 |
|---|---|---|---|---|
| Example 1 | 0.0086 | 0.004 | 0.010 | 25 |
| Example 2 | 0.0075 | 0.005 | 0.010 | 20 |
| Example 3 | 0.0081 | 0.004 | 0.011 | 20 |
| Comparative Example 1 | 0.0250 | 0.038 | 0.027 | 30 |
| Comparative Example 2 | 0.0320 | 0.041 | 0.032 | 35 |

*1Change amount after storage for one month at 50° C., 80% RH.
*2Light output decrease amount after exposure of X-ray amount corresponding to 10 years operation.

As described above, the ceramic scintillator array of the embodiment can improve the dimensional accuracy to cope with downsizing of the detector and the like while maintaining excellent light output, and can reduce the dimensional change amount (pitch shift of the segment, warpage of the scintillator array, variation in outside dimension) due to heating and cooling. Accordingly, it is possible to provide a ceramic scintillator array having an optimal dimensional accuracy and less temporal change and decrease in light output due to exposure to an X-ray even in an operating temperature range of the radiation inspection device such as the X-ray CT scanner. Further, using the ceramic scintillator array makes it possible to increase the resolution and the image accuracy and thereby provide a radiation detector and a radiation inspection device improved in medical diagnosis performance and non-destructive inspection accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes may be made without departing from the spirit of the inventions. The embodiments and modifications would fall within the scope and spirit of the inventions and fall within the inventions as set forth in accompanying claims and their equivalents.

What is claimed is:

1. A ceramic scintillator array comprising:
a plurality of scintillator segments each composed of a sintered compact of a rare earth oxysulfide phosphor; and
a reflective layer interposed between the scintillator segments adjacent to each other to integrate the plurality of scintillator segments, the reflective layer containing a transparent epoxy resin and reflective particles dispersed in the transparent epoxy resin, wherein the transparent epoxy resin is a two-component epoxy resin curable at room temperature;
wherein the reflective particles contain titanium oxide and at least one inorganic substance selected from the group consisting of alumina, zirconia, and silica; and
wherein a glass transition point of the transparent epoxy resin is 60° C. or higher, and a thermal expansion coefficient of the transparent epoxy resin at a temperature higher than the glass transition point is $2.5 \times 10^{-5}$/° C. or less.

2. The ceramic scintillator array according to claim 1, wherein the ceramic scintillator array is configured to minimize a change amount in any of a pitch of the ceramic scintillator segments, a warpage of the ceramic scintillator array, and an outside dimension of the ceramic scintillator array, whereby the change amount, after the ceramic scintillator array is stored in a packed state for one month in an atmosphere at a temperature of 50° C. and a relative humidity RH of 80%, is 0.02 mm or less.

3. The ceramic scintillator array according to claim 1, wherein the ceramic scintillator array is configured to minimize a decrease in light output of the ceramic scintillator array, wherein the decrease in light output, measured by an X-ray exposure amount corresponding to 10 years of operation, is within 25%.

4. The ceramic scintillator array according to claim 1, wherein a molecular structure of the transparent epoxy resin has a cyclo structure without any double bonds.

5. The ceramic scintillator array according to claim 1, wherein the transparent epoxy resin has an aliphatic skeleton.

6. The ceramic scintillator array according to claim 1, wherein the reflective layer contains, by mass ratio, 15% or more and 60% or less of the transparent epoxy resin and 40% or more and 85% or less of the reflective particles.

7. The ceramic scintillator array according to claim 1, wherein the rare earth oxysulfide phosphor has a composition expressed by a general formula $RE_2O_2S:Pr$,
wherein RE is at least one element selected from the group consisting of Y, Gd, La, and Lu, and wherein a content of Pr, relative to a content of $RE_2O_2S$, is 0.001 mol % or more and 10 mol % or less.

8. The ceramic scintillator array according to claim 7, wherein the rare earth oxysulfide phosphor contains a gadolinium oxysulfide phosphor containing Pr as an activator.

9. The ceramic scintillator array according of claim 1, wherein the reflective particles have a bimodal particle size distribution, wherein a first peak in the bimodal particle size distribution is 200 nm or more and 350 nm or less, and wherein a second peak in the bimodal particle size distribution is 750 nm or more and 1000 nm or less.

10. The ceramic scintillator array according to claim 1, wherein a reflection efficiency of the reflective layer with respect to light having a wavelength of 512 nm is 90% or more.

11. A radiation detector comprising the ceramic scintillator array according to claim 1.

12. A radiation inspection device comprising the radiation detector according to claim 11.

13. A method for manufacturing the ceramic scintillator array according to claim 1, the method comprising:
applying or filling a mixture of the reflective particles and an uncured material of the transparent two-component epoxy resin, having an absolute viscosity, measured in units of Pascal-second (Pa·s), of 0.2 Pa·s or more and 1 Pa·s or less, between the plurality of scintillator segments arrayed to constitute the ceramic scintillator array; and
curing the mixture at room temperature to form the reflective layer to thereby integrate the plurality of scintillator segments.

14. The method according to claim 13, wherein the transparent two-part epoxy resin has a total light transmittance of 85% or more.

* * * * *